United States Patent [19]

Jayne et al.

[11] 4,141,846

[45] Feb. 27, 1979

[54] LUBRICANT ADDITIVE

[75] Inventors: Gerald J. J. Jayne, Wokingham; Herbert F. Askew, Reading, both of England

[73] Assignee: Edwin Cooper and Company Limited, Bracknell, England

[21] Appl. No.: 777,774

[22] Filed: Mar. 15, 1977

[30] Foreign Application Priority Data

Mar. 26, 1976 [GB] United Kingdom ............... 12302/76

[51] Int. Cl.$^2$ ................................................. C10M 1/38
[52] U.S. Cl. .................................. 252/48.2; 252/47.5; 260/327 M; 260/327 TH; 260/455 B
[58] Field of Search ........ 260/455 B, 327 M, 327 TH; 252/48.2, 47.5

[56] References Cited

U.S. PATENT DOCUMENTS

| | | | |
|---|---|---|---|
| 3,369,979 | 2/1968 | Oswald et al. | 260/455 R |
| 3,607,945 | 9/1971 | Reece | 260/455 C X |
| 3,644,415 | 2/1972 | Neil et al. | 260/327 TH |
| 3,644,416 | 2/1972 | Neil et al. | 260/327 TH |
| 4,019,991 | 4/1977 | Jayne et al. | 252/48.2 |

*Primary Examiner*—Helen M. S. Sneed
*Attorney, Agent, or Firm*—Donald L. Johnson; Robert A. Linn; Joseph D. Odenweller

[57] ABSTRACT

New compounds are derived from intramolecular and intermolecular, in the case of a polymer, sulfur-bridged hydrocarbon rings containing from 6 to 12 carbon atoms. The hydrocarbon ring is preferably derived from 1,5-cyclooctadiene. The compounds also contain the residue of an alkoxyalkyl or aryloxyalkyl xanthate and may also contain the residue of a further nucleophilic group. The new compounds are useful in lubricating oil compositions. The compositions may also contain other conventional lubricant additives.

24 Claims, No Drawings

LUBRICANT ADDITIVE

BACKGROUND OF THE INVENTION

As described in our U.S. Pat. Application Ser. No. 553,738, filed Feb. 27, 1975, now U.S. Pat. No. 4,019,991 alkyl xanthates of intramolecular sulfur-bridged cyclic hydrocarbons are effective multi-purpose additives for lubricating oils. Of these, the lower alkyl derivatives are the most effective. One detriment these lower alkyl derivatives have is the presence of an unpleasant odor. The present invention is directed at novel xanthates which, while possessing in general as good or better effectiveness, do not exhibit noticeable unpleasant odor.

SUMMARY OF THE INVENTION

The invention relates to lubricant additives and in particular to sulfur-containing additives. The present invention relates more particularly to sulfur-containing lubricating oil additives which are alkoxyalkyl or aryloxyalkyl xanthates of intramolecular sulfur-bridged cyclic hydrocarbons. According to the present invention there is provided a compound or mixture of compounds of the formula:

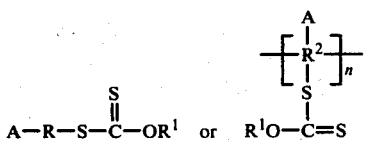

(I)     (II)

wherein in Formula (I) R is the residue of an intramolecular sulfur-bridged hydrocarbon ring containing from 6 to 12 carbon atoms or wherein in Formula

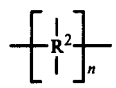

(II)

is a polymer comprising the residue of a plurality of substantially intermolecularly sulfur-bridged hydrocarbon rings each containing from 6 to 12 carbon atoms, n being the degree of polymerization, each $R^1$ is the same or different and is an alkyl or alkenyl group, preferably containing from 1 to 20, (e.g. methyl, ethyl, propyl, n-butyl, isobutyl, 1-methylheptyl, 2-ethylhexyl, n-dodecyl, n-hexadecyl, sec-eicosyl and the like) more particularly 2 to 12, carbon atoms; an aralkyl group, preferably benzyl or alkylbenzyl containing 8-20 carbon atoms (e.g. 4-methylbenzyl, 2,4-di-tert-butylbenzyl, α-methylbenzyl, α,α-dimethylbenzyl and the like) or an alkoxyalkyl or aryloxyalkyl group having the formula $+R^4O+_mR^5$ wherein $R^4$ is a divalent alkylene radical containing 2-6 carbon atoms, $R^5$ is an alkyl radical containing 1 to 6 carbon atoms or an aryl radical containing 6 to 10 carbon atoms, and m is an integer from 1 to 6, at least one of $R^1$ being said alkoxyalkyl or aryloxyalkyl group, and A is a nucleophilic group. In a more preferred embodiment the additive is a mixture of xanthate compounds in which at least about 20 mole percent of $R^1$ is alkoxyalkyl. In a highly preferred embodiment $R^1$ is selected from alkyl and alkoxyalkyl, the mole ratio of alkyl to alkoxyalkyl being 1 to 4:1, more preferably 2 to 4:1. R and

are preferably derived from monocyclic olefins such as 1,3,5-cycloheptatriene, cyclooctatetraene, 1,3-cyclooctadiene, 1,5-cyclooctadiene, or 3-alkoxy derivatives thereof and 1,5,9-cyclododecatriene, especially the cis-trans-trans version thereof. The sulfur-bridging of these hydrocarbons is achieved by reacting with sulfur dichloride or other sulfur chloride compound to yield either monomeric or polymeric derivatives. The sulfur bridges may be oxidized to carry one or two oxygens to give a sulfone or sulfoxide.

The group A preferably has the formula:

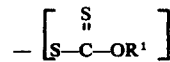

wherein $R^1$ is as defined above and wherein the two groups $R^1$ may be the same or different. Preferably R is the group

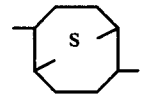

and $R^1$ is said alkoxyalkyl group.

Alternatively, the group A may have the formula:

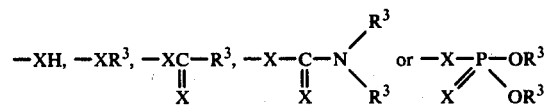

wherein X is oxygen or sulfur and $R^3$ is an alkyl, aryl, alkaryl or aralkyl group.

Preferably, the alkyls contain 1-12 carbon atoms (e.g., methyl, ethyl, hexyl, dodecyl), the aryls contain 6-12 carbon atoms (e.g., phenyl, naphthyl), the alkaryls contain 7-12 carbon atoms (e.g., 4-methylphenyl, 4-sec-butylphenyl, 3,5-di-isopropylphenyl), and the aralkyl group contains 7-12 carbon atoms (e.g., benzyl, phenethyl, 3-phenylpropyl, 2-naphthylethyl). Further alternatives for A include —CN and —NCS.

The invention also includes a lubricating oil composition which comprises a lubricating oil and compounds as defined above. Such compositions may be employed directly as lubricants, in which case the novel compounds of the present invention will be present in minor amounts, preferably in an amount from 0.01 to 10% by weight, more particularly from 0.3 or 0.5 to 3% by weight. The number of carbon atoms in the, or each, group $R^1$, and the, or each, group $R^3$ if present, should be sufficiently high to render the compounds oil soluble. On the other hand, it is desirable that the number of carbon atoms in the groups $R^1$ and $R^3$ should not be too high since it is believed that the sulfur in the molecule is the active component, otherwise large amounts of the compounds would have to be used to give equivalent sulfur contents. Particularly preferred additives in this respect are compounds in which A is a group of the formula:

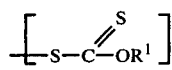

and in which groups $R^1$ are a mixture of both alkoxyalkyl and alkyl groups. In this embodiment a particularly preferred alkyl is sec-octyl, e.g., 1-methylheptyl, in which the mole ratio of alkyl to alkoxyalkyl group is about 1:1.

The term lubricating oil composition also includes the materials known in the art as oil concentrates and additive packages, i.e., concentrated solutions in lubricating oil, optionally together with one or more conventional additives intended to be diluted with further quantities of oil to form the final lubricant. In this case the novel compounds of the present invention may be present in a wide range of proportions, e.g., 10% to 90%. In general, such concentrated solutions will normally contain from 20% to 50% by weight of the novel compounds of the present invention. The lubricating oil used in the lubricants, or the concentrates or packages, may be any of the well-known oils of appropriate viscosity characistics and may consist of or include synthetic oils.

The sulfur-bridged compounds may be prepared by reacting sulfur dichloride with the unsaturated ring compound, preferably in an inert solvent at a temperature between $-20°$ and $100°$ C. to give a dichloro intramolecular sulfur-bridged derivative. Details of the preparations of these compounds are given in J. Org. Chem. 33, page 2627 (1966); J. Org. Chem. 31, pages 1679 and 1669 (1966), incorporated herein by reference.

The compounds of the present invention may then be prepared by reacting the metal, preferably the alkali metal, e.g. sodium, or especially potassium, salt of an alkyl, alkenyl, aralkyl, aryloxyalkyl or alkoxyalkyl xanthate with the dichloro sulfur-bridged compound. When carried out in the ratio of about two moles of xanthate to one mole of dichloro sulfur-bridged compound, compounds of the formula:

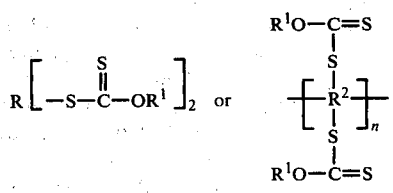

are obtained wherein R, $R^1$, $R^2$ and n have the same significance as above.

When the xanthate and the dichloro sulfur-bridged compound are reacted in a mole ratio of about 1:1, one chlorine remains unreacted. This chlorine atom can then be reacted with a metal derivative of the nucleophilic group A.

The invention therefore includes as intermediates compounds having the formulae

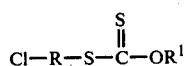

and

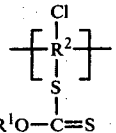

wherein R, $R^1$ and

have the same significance as above.

Alternatively, the metal derivative of the nucleophilic group A may be reacted with the dichloro sulfur-bridged compound which may then be reacted with the xanthate.

In some cases, such as when the starting hydrocarbon ring compound contains 3 or more double bonds (e.g., cyclododecatriene), the compounds of the invention may possess residual reactive ethylenically unsaturated double bonds which may be reacted with compounds reactive therewith. Such compounds reacting with residual unsaturation include sulfur, phosphorus, pentasulfide, mercaptans, phenols, thiocyanate anions, thiophenols and carboxylic acids. Specific examples of such compounds are mercaptans and carboxylic acids containing from 1 to 16 carbon atoms; phenol (unsubstituted) and thiophenol (unsubstituted). The foregoing compounds may be reacted with the residual unsaturation at a temperature of from $50°$ to $200°$ C. It may be desirable to use a catalyst known to promote their reaction with ethylenically unsaturated double bonds, such as mineral acids or Lewis acid catalysts such as boron trifluoride, the etherate or phenolate complex thereof or amines.

It will be understood that the lubricating compositions of the present invention may also contain, if desired, conventional lubricant additives such as ancillary antioxidants and antiwear additives (preferably ashless), corrosion inhibitors, dispersants, particularly dispersants of the succinimide type, detergents, thickeners, pour-point depressants and viscosity index improvers. Numerous examples of such conventional additives are described in U.K. Patent Specification No. 1,205,177 and the various documents referred to therein.

A further aspect of the invention is a process for preparing a compound of formula:

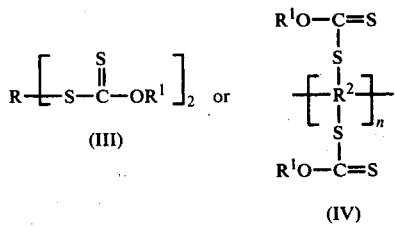

in which $R^1$ is an alkoxyalkyl or aryloxyalkyl group having the formula:

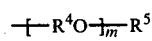    V wherein R, $R^2$, $R^4$, $R^5$, m and n are as previously defined, which process comprises reacting a metal salt of an alkoxyalkyl xanthate or an aryloxyalkyl xanthate having the formula:

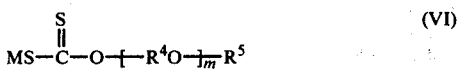

$$\text{MS}-\overset{\overset{\text{S}}{\|}}{\text{C}}-\text{O}-[-R^4\text{O}-]_m R^5 \quad (\text{VI})$$

in which M is a metal, preferably an alkali metal, with a dichloro sulfur-bridged compound of formula Cl-R-Cl or

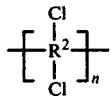

wherein R, $R^2$ and n are previously defined in the ratio of about two moles of xanthate to one mole of said dichloro sulfur-bridged compound.

In another preferred embodiment $R^1$ is a mixture of alkoxyalkyl groups of Formula (V) and alkyl groups containing 2-12 carbon atoms. Preferably the mole ratio of alkyl groups to alkoxyalkyl groups is from about 1 to 4:1, more preferably 1:1. In this embodiment both the metal salt of an alkoxyalkyl xanthate of Formula (VI) and a metal salt of an alkyl xanthate are reacted with Cl-R-Cl or

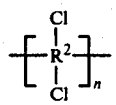

Preferably the metal salts of the alkoxyalkyl xanthate are the alkali metal salts such as the Na or K salts.

The preferred R and $R^2$ groups are those derived from cyclic polyenes by reaction with $SCl_2$. Examples of such cyclic polyenes are cycloheptatriene, cyclooctadiene, cyclododecatriene, and the like. The preferred R is formed by reacting 1,5-cyclooctadiene with $SCl_2$ to form 2,6-dichloro-9-thiabicyclo(3,3,1)-nonane. The preferred $R^2$ is formed by reacting $SCl_2$ with 1,5,9-cyclododecatriene.

Examples of alkoxyalkyl groups include methoxyethyl, ethoxyethyl, 2-methoxypropyl, 2-ethoxypropyl, methoxyethoxyethyl, 2-methoxybutyl, and the like. These are derived from the well-known monoalkyl ethers of alkylene glycols and polyglycols. Examples of aryloxyalkyl groups include phenoxyethoxyethyl, phenoxyethyl and toloxypropoxypropoxypropyl.

A further embodiment of the invention is a process for preparing a compound of Formula (I) or (II) which comprises reacting an alkoxyalkyl or an aryloxyalkyl xanthate having Formula (VI) with a dichloro sulfur-bridged compound of formula Cl-R-Cl or

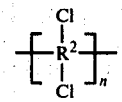

in about a 1:1 mole ratio and reacting the intermediate product so formed with a metal salt of the nucleophilic group A in about a 1:1 mole ratio. Alternatively, this reaction sequence may be reversed so that the metal salt of group A is reacted first followed by the alkoxyalkyl or aryloxyalkyl xanthate having Formula (IV) or metal salt thereof.

There now follows by way of example a description of the preparation of typical compounds in accordance with the present invention.

EXAMPLE I

In a reaction flask was placed 600 ml of the monoethyl ether of ethylene glycol and 144.9 g of 85% KOH. While stirring, this mixture was heated to 80° C. to dissolve the KOH. The solution was cooled to about 40° C. and 167.2 g of $CS_2$ added dropwise with cooling. A precipitate formed and toluene was added as required to maintain fluidity. Following this, a solution of 211 g of 2,6-di-chloro-9-thiabicyclo(3,3,1)-nonane (prepared by reacting equal mole amounts of $SCl_2$ and 1,5-cyclooctadiene in methylene chloride solvent at $-5°$ - $0°$ C.) in 800 ml of toluene was added and the mixture stirred at 75° C. for 3 hours. The reaction product was washed with water to remove precipitated salts and then dried over anhydrous Mg $SO_4$. The solvent was distilled out in a rotary evaporator to give the product, 2,6-bis-(ethoxyethoxythiocarbonylthio)-9-thiabicyclo(3,3,1) nonane in 86% yield; anal. 31.5% sulfur, 0.46% chlorine.

Following the above general procedure, a series of compounds were prepared using the following glycol ethers:

TABLE 1

| EXAMPLE | GLYCOL ETHER |
|---|---|
| II | ethyleneglycol monomethyl ether |
| III | ethyleneglycol monoisopropyl ether |
| IV | ethyleneglycol monobutyl ether |
| V | diethyleneglycol monoethyl ether |
| VI | diethyleneglycol monobutyl ether |
| VII | propyleneglycol monomethyl ether |
| VIII | dipropyleneglycol monomethyl ether |
| IX | tripropyleneglycol monomethyl ether |

These examples gave compounds having the following structure:

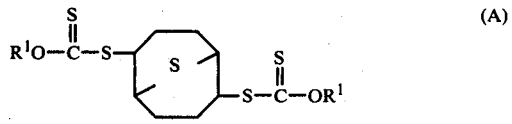

$R^1$, yield and analysis were as follows:

TABLE 2

| Example | $R^1$ | Yield | S% | Cl% |
|---|---|---|---|---|
| II | $-CH_2CH_2OCH_3$ | 69 | 33.6 | 0.42 |
| III | $-CH_2CH_2OCH(CH_3)_2$ | 80 | 31.1 | 0.28 |
| IV | $-CH_2CH_2OC_4H_9$ | 88 | 29.3 | 0.38 |
| V | $-(CH_2CH_2O)_2-C_2H_5$ | 78 | 29.5 | 0.36 |
| VI | $-(CH_2CH_2O)_2C_4H_9$ | 56 | 24.9 | 0.29 |
| VII | $-CH_2CH(CH_3)OCH_3$ | 87 | 32.1 | 0.60 |
| VIII | $-[CH_2CH(CH_3)O]_2CH_3$ | 64 | 26.1 | 1.55 |
| IX | $-[CH_2CH(CH_3)O]_3CH_3$ | 88 | 20.6 | 0.26 |
| X | Mixture of 1-methylheptyl and ethoxyethyl 1:1 ratio | 74 | 28.3 | 0.34 |
| XI | Mixture of 1-methylheptyl and methoxypropyl 1:1 ratio | 87 | 28.9 | 0.44 |

Further compounds were prepared having the structure:

(B)

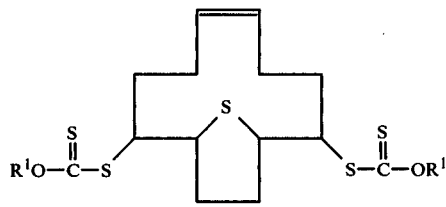

wherein $R^1$ is as previously described. In Example XII $R^1$ was the group ethoxyethyl. The yield was 72% and the product analyzed 26.8% S and 0.5% Cl.

EXAMPLE XIII

In a reaction flask were placed 52.8 g (0.25 mol) of 2,6-dichloro-9-thiabicyclo(3,3,1) nonane, prepared as in Example 1, 7.8 g (0.125 mol) of ethylene glycol and 100 ml of toluene. The mixture was heated in a current of nitrogen for two periods of 7 hours at 80° C., followed by two periods of 7 hours at 100° C., by which time evolution of HCl had virtually ceased.

Potassium isopropyl xanthate was prepared by reacting 22.8 g (0.3 mol) of $CS_2$ with a solution of 19.8 g 85% KOH (0.3 mol) in 100 ml of isopropanol and 100 ml of toluene. This was then added to the first reaction product and the mixture was heated to 78° C. for 3 hours. More toluene was then added, and the product washed with water, dried and stripped, yielding a brown viscous liquid in 85.5% yield. This product, which was believed to have the formula

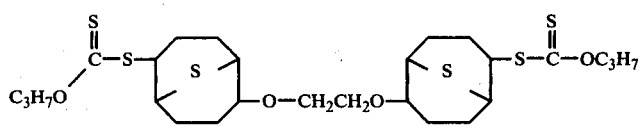

contained 31.3% S (theory 31.5%) and 0.72% Cl.

Other derivatives can be made using any of a broad series of glycol ethers such as:
1,4-butyleneglycol monohexyl ether
1,6-hexyleneglycol monomethyl ether
triethyleneglycol monopentyl ether
tetrapropyleneglycol monohexyl ether
hexaethyleneglycol monomethyl ether
and the like, including mixtures thereof as well as mixtures with alcohols.

Several of the above compounds were subjected to a Copper Corrosion Test (Copper Strip Test ASTM-D 130-68; IP 154/69). Examples I-X and XII and XIII were subjected to the test and all gave a 1b rating.

Several of the compounds were subjected to a 36-hour Petter W-1 engine test (IP 176/69) but the procedure was slightly amended in that the oil sample removed at 16 hours was not replaced by new oil. In this test the lubricating oil was blended to contain 1% by weight of the test additive in a formulated mineral lubricating oil which contained other conventional oil additives (e.g., succinimide dispersant, overbased magnesium sulfonate, zinc dialkyldithiophosphate, etc.). All the test additives except Examples XII and XIII were dixanthates of Formula (A) and were derived from 2,6-dichloro-9-thiabicyclo(3,3,1) nonane but differed in the group $R^1$ attached to the xanthate oxygen. Several alkyl xanthate are included for comparison. Test criteria are the bearing weight loss and the piston rating on a scale from 0-10 (10 = clean).

TABLE 3

| Xanthate O substituent | Bearing Wt. loss (mg) | Piston Rating skirt | Piston Rating undercrown |
|---|---|---|---|
| bis-isopropyl | 6 | 8.5 | 5.1 |
| ethyl/isopropyl | 8 | 10.0 | 7.9 |
| ethyl/sec-butyl | 10 | 9.4 | 0.1 |
| bis (4-methyl pentyl-2) | 21 | 8.3 | 2.0 |
| bis(sec-octyl) | 14 | 9.6 | 6.6 |
| Example I | 8 | 9.9 | 9.0 |
| Example II | 18 | 9.9 | 9.0 |
| Example III | 14 | 9.6 | 7.1 |
| Example IV | 16 | 9.8 | 9.1 |
| Example VII | 25 | 10.0 | 10.0 |
| Example VIII | 8 | 9.9 | 8.7 |
| Example IX | 4 | 10.0 | 8.0 |
| Example X | 6 | 10.0 | 9.9 |
| Example XI | 13 | 9.9 | 7.0 |
| Example XII | 11 | 9.8 | 7.5 |
| Example XIII | 12 | 9.9 | 5.4 |

As the above test results show, the alkoxyalkyl xanthates of this invention are exceptionally effective in maintaining piston cleanliness. They are substantially more effective than similar alkyl xanthates, especially in regard to piston undercrown rating. Appearance of the bearings in all cases was very good, being light straw to brown with no sign of pitting or corrosion. In addition, they do not have a disagreeable odor as usually is encountered with lower alkyl xanthates.

The additives were also tested by the Rotary Bomb Oxidation Test (IP 229/73) to further determine their antioxidant effectiveness. In this test, oil, water and a copper coil are placed in a test bomb which is pressurized to 90 psi with oxygen. The bomb is placed in a constant temperature bath at 150° C. and rotated. Test criterion is minutes until 25 psi pressure drop. Results obtained with the blank oil and the same oil containing the present additives are shown in the following table.

TABLE 4

| Additive of | Minutes to Failure |
|---|---|
| Blank | 40 |
| Example I | 100 |
| Example II | 105 |
| Example III | 85 |
| Example V | 120 |
| Example VI | 90 |
| Example VII | 42 |
| Example VIII | 20 |
| Example IX | 54 |

The EP properties of the additives were demonstrated by subjecting several of them to the Timken O.K. Load Test. In this test, one member is rotated against another member under increasing load. Their contact area is lubricated with oil containing the test additive. The Timken O.K. load is the maximum load at which no scoring or seizure occurs.

TABLE 5

| Additive of | Timken O.K. Load (lbs) |
|---|---|
| Blank | 12 |
| Example I | 45 |
| Example IV | 24 |

TABLE 5-continued

| Additive of | Timken O.K. Load (lbs) |
|---|---|
| Example IX | 18 |

The present additives are useful in a broad range of lubricating oils including both mineral and synthetic oils. Synthetic oils includes such materials as decene oligomer (mainly trimer), alkyl aromatics (e.g., didodecyl benzene), olefin polymers and copolymers, and the like. They are also useful in synethetic esters oils such as the 2-ethylhexanol ester of adipic acid, the $C_{6-9}$ alkanoic acid ester of trimethylolpropane, complex esters derived from ethyleneglycol-sebacic acid-hexanoic acid, and any of the other well-known ester lubricants. Mixtures of mineral oil and synthetic lubricants are also contemplated for use with the present additives. In addition, the additives are useful in other lubricating compositions such as gear lubricants and greases.

In further embodiments the xanthate is a glycol or polyglycol xanthate. These additives are made according to the methods previously described, but glycols or polyglycols are used in place of the monoethers of glycol or polyglycol. The glycol or polyglycol is first used to prepare the alkali metal xanthate by reaction of alkali metal hydroxide (e.g., KOH) and glycol or polyglycol with $CS_2$ to form a xanthate intermediate of the following general formula:

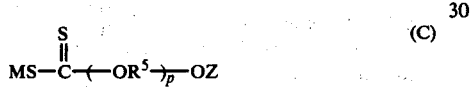
(C)

wherein M is an alkali metal (e.g., K, Na), $R^5$ is a divalent alkylene radical containing 2-4 carbon atoms, p is an integer from 1 to about 6, and Z is hydrogen or the group:

(D)

depending upon the ratio of reactants.

Useful glycols include ethyleneglycol, diethyleneglycol, triethyleneglycol, tetraethyleneglycol, propyleneglycol, dipropyleneglycol, tripropyleneglycol, polyalkyleneglycol containing both ethylene and propylene units, and the like, including mixtures thereof.

Reaction of glycol intermediate (C) with a di-halo intramolecularly-bridged cyclic hydrocarbon will then form the following types of compounds.

When Z in Formula (C) is hydrogen, compounds having the following structure will form:

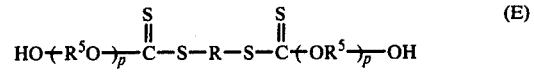
(E)

When Z is the group (D), compounds having the following structure will form:

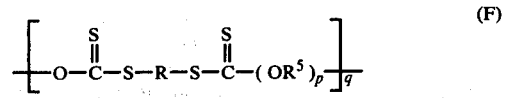
(F)

wherein q is the degree of polymerization ranging up to about 5.

In a further embodiment, a mixture of glycol xanthate (C) with an alkyl or alkoxyalkyl xanthate can be used. This will give a reaction mixture containing alkyl and/or alkoxyalkyl groups attached to xanthate oxygen and glycol residues attached to xanthate oxygen with the xanthate group bonded to an intramolecularly sulfurbridged cyclic hydrocarbon.

When the glycol xanthate used in the mixture of xanthates has Formula (C), in which Z is hydrogen, the resultant compounds can be illustrated by the following formula:

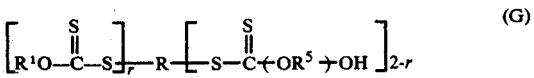
(G)

wherein R and $R^1$ are as previously defined and r has an average value ranging from about 0.2 to about 1.8. The value of r depends on the molar portion of each type of xanthate used.

Preferably, the different xanthate types are reacted sequentially such as first reacting one mole of potassium alkoxyalkyl or alkyl xanthate with one mole of 2,6-dichloro-9-thiabicyclo(3,3,1) nonane and then reacting one mole of potassium glycol xanthate of Formula (C) (Z = H) with the preformed intermediate to form the compound:

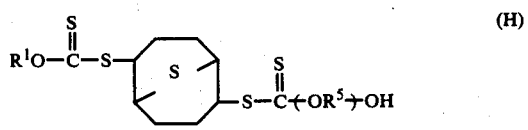
(H)

Alternatively, one mole of the glycol xanthate of Formula (C) (Z = group D) can be reacted with 2 moles of 2,6-di-chloro-9-thiabicyclo(3,3,1) nonane followed by reaction with 2 moles of potassium alkyl and/or alkoxyalkyl xanthate to form the compound:

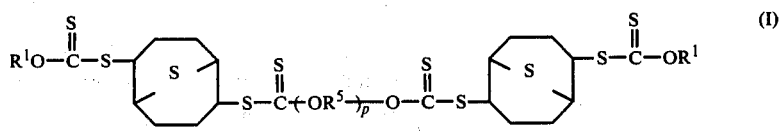
(I)

By proper selection of reactant ratio glycol-centered polymeric compounds can be prepared having an alkyl or alkoxyalkyl xanthate terminal group. The following formula illustrates these compounds:

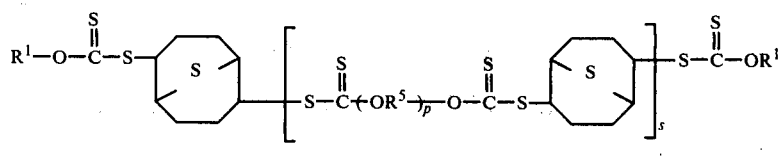

wherein s determines the length of the polymer and can range from 1 to about 6.

In general, the above compounds are obtained in a reaction mixture as the product formed by the process comprising reacting:
(a) an alkali metal group xanthate having Formula (C) with
(b) a di-halo intramolecularly sulfur-bridged cyclic hydrocarbon and, optionally,
(c) an alkali metal akyl alkoxyalkyl or aryloxyalkyl xanthate having formula

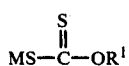

wherein M is an alkali metal and $R^1$ is as previously defined.

The above glycol xanthate derivatives of intramolecularly sulfur-bridged cyclic hydrocarbons are used as lubricating oil additives in the same manner as the previously described alkoxyalkyl xanthate derivatives. Some of the glycol xanthates have limited solubility in mineral oil but do have adequate solubility in synthetic ester lubricants and, in addition, can be used in gear lube formulations and in greases. It is to be understood that the invention also includes such gear lube formulations and greases.

A preferred lubricating composition comprises a major amount of a lubricating oil and from 0.5 to 3% by weight a compound having the formula:

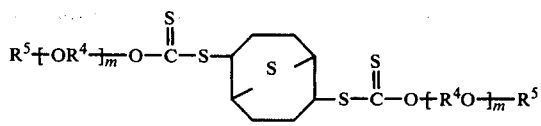

wherein $R^4$ and $R^5$ are as defined above.

We claim:
1. A compound or mixture of compounds having the formula

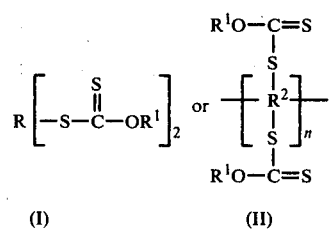

wherein in Formula (I) R is the residue of an intramolecular sulfur-bridged hydrocarbon ring containing from 6 to 12 carbon atoms or wherein in Formula

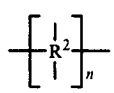

is a polymer comprising the residue of a plurality of n substantially intermolecularly sulfur-bridged hydrocarbon rings each containing from 6 to 12 carbon atoms, n being the degree of polymerization, each $R^1$ is the same or different and is an alkyl, alkenyl, aralkyl, aryloxyalkyl or an alkoxyalkyl group having the formula $[R^4O]_m R^5$ wherein $R^4$ is a divalent alkylene radical containing 2-6 carbon atoms, $R^5$ is an alkyl radical containing 1-6 carbon atoms or an aryl radical containing 6-10 carbon atoms, and m is an integer from 1-6, at least about 20 mole percent of $R^1$ being said aryloxyalkyl or alkoxyalkyl group.

2. A compound of claim 1 having Formula (I) wherein R is the group

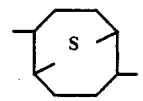

and $R^1$ is selected from said alkyl groups and alkoxyalkyl groups, the mole ratio of alkyl to alkoxyalkyl groups being about 1-4:1.

3. A compound of claim 1 wherein R or

is derived from an unsaturated ring compound selected from the group consisting of 1,3,5-cycloheptatriene, cyclooctatetraene, 1,3-cyclooctadiene, 1,5-cyclooctadiene and 3-alkoxy derivatives thereof, and cis, trans, trans-1,5,9-cyclododecatriene.

4. A compound of claim 1 having Formula (I) wherein R is the group

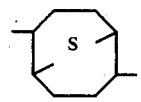

and $R^1$ is said alkoxyalkyl group.

5. A compound of claim 4 wherein said alkoxyalkyl group is $-CH_2-CH_2-O-CH_3$.

6. A compound of claim 4 wherein said alkoxyalkyl group is $-CH_2-CH_2-O-CH_2-CH_3$.

7. A compound of claim 4 wherein said alkoxyalkyl group is

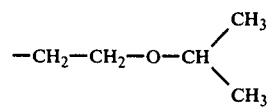

8. A compound of claim 4 wherein said alkoxyalkyl group is $-CH_2-CH_2-O-C_4H_9$.

9. A compound of claim 4 wherein said alkoxyalkyl group is $$-CH_2-CH(CH_3)-O-CH_3.$$

10. A compound of claim 4 wherein said alkoxyalkyl group is $$\text{\textpm}CH_2-CH(CH_3)-O\text{\textpm}_2-CH_3.$$

11. A compound of claim 4 wherein said alkoxyalkyl group is $$\text{\textpm}CH_2-CH(CH_3)-O\text{\textpm}_3-CH_3.$$

12. A compound of claim 1 wherein $R^1$ is selected from said alkyl groups and said alkoxyalkyl groups, the mole ratio of alkyl to alkoxyalkyl groups being about 1 to 4:1.

13. A compound of claim 12 wherein said alkyl groups are sec-octyl.

14. A compound of claim 2 wherein said alkyl groups are sec-octyl.

15. A compound of claim 14 having Formula (I) wherein $R^1$ is selected from 1-methylheptyl and methoxypropyl in the mole ratio of about 1:1.

16. A compound of claim 14 having Formula (I) wherein $R^1$ is selected from 1-methylheptyl and ethoxyethyl in the mole ratio of about 1:1.

17. A lubricating oil composition comprising a major amount of a lubricating oil and a minor amount of a compound or mixture of compounds having the formula $$R\left[-S-\overset{S}{\underset{\|}{C}}-OR^1\right]_2 \quad \text{or} \quad \left[\begin{array}{c} R^1O-C=S \\ | \\ S \\ | \\ R^2 \\ | \\ S \\ | \\ R^1O-C=S \end{array}\right]_n$$

(I)      (II)

wherein in Formula (I) R is the residue of an intramolecular sulfur-bridged hydrocarbon ring containing from 6 to 12 carbon atoms or wherein in Formula $$\left[\begin{array}{c} | \\ R^2 \\ | \end{array}\right]_n \quad (II)$$

is a polymer comprising the residue of a plurality of n substantially intermolecularly sulfur-bridged hydrocarbon rings each containing from 6 to 12 carbon atoms, n being the degree of polymerization, each $R^1$ is the same or different and is an alkyl, alkenyl, aralkyl, aryloxyalkyl or an alkoxyalkyl group having the formula $[R^4O]_mR^5$ wherein $R^4$ is a divalent alkylene radical containing 2-6 carbon atoms, $R^5$ is an alkyl radical containing 1-6 carbon atoms or an aryl radical containing 6-10 carbon atoms, and m is an integer from 1-6, at least about 20 mole percent of $R^1$ being said aryloxyalkyl or alkoxyalkyl group.

18. A lubricating oil composition of claim 17 containing from 0.01–10% by weight of said compound or mixture of compounds.

19. A lubricating oil composition of claim 18 containing from 0.05–3% by weight of said compound or mixture of compounds.

20. A lubricating oil composition of claim 19 wherein said compound or mixture of compounds has the formula:

$$R^5\text{\textpm}OR^4\text{\textpm}_m O-\overset{S}{\underset{\|}{C}}-S-\underset{}{\bigcirc}-S-\overset{S}{\underset{\|}{C}}-O\text{\textpm}R^4O\text{\textpm}_m R^5$$

wherein $R^4$ is a divalent alkylene radical containing 2-6 carbon atoms, $R^5$ is an alkyl radical containing 1-6 carbon atoms or an aryl radical containing 6-10 carbon atoms and m is an integer from 1-6.

21. A lubricating composition comprising a major amount of a lubricating oil and a minor amount of a compound or mixture of compounds of claim 12.

22. A lubricating composition of claim 21 wherein said alkyl groups are sec-octyl.

23. A lubricating composition comprising a major amount of lubricating oil and a minor amount of a compound or mixture of compounds of claim 15.

24. A lubricating composition comprising a major amount of a lubricating oil and a minor amount of a compound or mixture of compounds of claim 16.

* * * * *